US012778574B2

(12) United States Patent
Binmoeller et al.

(10) Patent No.: US 12,778,574 B2
(45) Date of Patent: Nov. 3, 2026

(54) SINGLE-ANCHOR MECHANISM AND SUTURING DEVICE

(71) Applicants: MICRO-TECH (NANJING) CO., LTD., Jiangsu (CN); Kenneth F. Binmoeller, Rancho Santa Fe, CA (US); Qiang Zhang, Guangzhou (CN)

(72) Inventors: Kenneth F. Binmoeller, Rancho Santa Fe, CA (US); Qiang Zhang, Guangzhou (CN); Hongyan Jin, Jiangsu (CN); Xiaojun Ma, Jiangsu (CN)

(73) Assignees: MICRO-TECH (NANJING) CO., LTD., Jiangsu (CN); Kenneth F. Binmoeller; Qiang Zhang, Guangdong (CN)

( * ) Notice: Subject to any disclaimer, the term of this patent is extended or adjusted under 35 U.S.C. 154(b) by 182 days.

(21) Appl. No.: 18/797,420

(22) Filed: Aug. 7, 2024

(65) Prior Publication Data

US 2025/0057524 A1 Feb. 20, 2025

(30) Foreign Application Priority Data

Aug. 15, 2023 (CN) ........................ 202311025032.2

(51) Int. Cl.
*A61B 17/04* (2006.01)

(52) U.S. Cl.
CPC ...... *A61B 17/0401* (2013.01); *A61B 17/0469* (2013.01); *A61B 17/0487* (2013.01); *A61B 2017/0488* (2013.01)

(58) Field of Classification Search
CPC ............ A61B 17/0401; A61B 17/0467; A61B 17/0469; A61B 17/0487; A61B 17/0491; A61B 2017/0409; A61B 2017/0441; A61B 2017/0488; A61B 2017/0649
See application file for complete search history.

(56) References Cited

U.S. PATENT DOCUMENTS

| | | | | |
|---|---|---|---|---|
| 7,087,064 | B1 * | 8/2006 | Hyde .................... | A61F 2/2445 606/232 |
| 2007/0049942 | A1 * | 3/2007 | Hindrichs ............. | A61F 2/2451 623/13.14 |
| 2007/0244555 | A1 * | 10/2007 | Rafiee ................... | A61F 2/2445 623/2.11 |
| 2010/0280605 | A1 * | 11/2010 | Hammer ............... | A61F 2/2436 623/2.11 |
| 2011/0106247 | A1 * | 5/2011 | Miller ................... | A61F 2/2445 623/2.17 |
| 2011/0288635 | A1 * | 11/2011 | Miller ................... | A61F 2/2457 606/228 |

(Continued)

*Primary Examiner* — Diane D Yabut
*Assistant Examiner* — Christian D Knauss
(74) *Attorney, Agent, or Firm* — BCF LLP

(57) ABSTRACT

The present disclosure provides a single-anchor mechanism and a suturing device. The single-anchor mechanism provided in the present disclosure includes: an anchor, a transmission tube, a traction wire, and a limiting element; one end of the traction wire is connected to the anchor, and the traction wire passes through the transmission tube; an end portion of the anchor opposite to the transmission tube is provided with an engaging portion adapted; the limiting element is connected to the traction wire, and the limiting element abuts against an end portion of the transmission tube away from the anchor.

17 Claims, 9 Drawing Sheets

(56) References Cited

U.S. PATENT DOCUMENTS

| | | | | |
|---|---|---|---|---|
| 2012/0053629 | A1* | 3/2012 | Reiser | A61B 17/0485 606/232 |
| 2014/0114390 | A1* | 4/2014 | Tobis | A61F 2/2466 623/1.11 |
| 2015/0366556 | A1* | 12/2015 | Khairkhahan | A61F 2/2454 606/232 |
| 2018/0028180 | A1* | 2/2018 | Binmoeller | A61B 17/0467 |
| 2019/0216601 | A1* | 7/2019 | Purcell | A61F 2/2454 |
| 2020/0178956 | A1* | 6/2020 | Mitelberg | A61B 17/0401 |
| 2023/0069080 | A1* | 3/2023 | Rao | A61B 17/04 |

* cited by examiner

SINGLE-ANCHOR MECHANISM AND SUTURING DEVICE

CROSS-REFERENCE TO RELATED APPLICATION

The present disclosure claims priority to Chinese patent application CN202311025032.2, titled "SINGLE-ANCHOR MECHANISM AND SUTURING DEVICE", filed on Aug. 15, 2023, the entire contents of which are incorporated herein by reference as part of the present disclosure.

TECHNICAL FIELD

The present disclosure relates to the technology field of medical suturing, and in particular to a single-anchor mechanism and a suturing device.

BACKGROUND ART

When using a helical anchor to connect the traction wire, it is typically necessary to use a spring tube to drive the anchor to rotate, thereby allowing the helical anchor to engage and drill into the tissue to be sutured. In the prior art, to ensure the transmission between the spring tube and the anchor, it is necessary to connect the anchor to the spring tube and use a key or pin for circumferential limitation. After the anchor is fixed, to facilitate the operation of the traction wire, the spring tube needs to be withdrawn, which requires disengaging the spring tube from the anchor. The operator needs to apply external force to bend or damage the key or pin to cause it to fail. This not only makes the instrument structure difficult to process and assemble, leading to high manufacturing costs of the device, but also requires significant operating force to separate the helical anchor from the spring tube, making the withdrawal of the spring tube inconvenient.

SUMMARY

The objective of the present disclosure is to provide a single-anchor mechanism and a suturing device to solve the technical problems of high assembly difficulty in the single-anchor mechanism and inconvenient withdrawal of transmission tubes in the prior art.

In a first aspect, the single-anchor mechanism provided in the present disclosure includes: an anchor, a transmission tube, a traction wire, and a limiting element;

- one end of the traction wire is connected to the anchor, and the traction wire passes through the transmission tube;
- an end portion of the anchor opposite to the transmission tube is provided with an engaging portion adapted; and
- the limiting element is connected to the traction wire, and the limiting element abuts against an end portion of the transmission tube away from the anchor.

In one optional embodiment, the limiting element includes a polymer elastic component, and the polymer elastic component is provided with a wire-clamping portion.

The traction wire is interference-fitted into the wire-clamping portion.

The polymer elastic component abuts against the end portion of the transmission tube away from the anchor.

In one optional embodiment, the transmission tube includes a spring tube and an engaging member, wherein the engaging member is connected to the spring tube.

In one optional embodiment, the engaging portion includes a first insertion portion provided on the engaging member, and the first insertion portion is adapted to a proximal end of the anchor.

In one optional embodiment, the single-anchor mechanism further comprises a handle and a rotating wheel.

The transmission tube passes through the handle, the transmission tube is connected to the rotating wheel, and the rotating wheel is coaxial with the transmission tube.

In one optional embodiment, the handle is provided with a stopping and limiting element, and the stopping and limiting element abuts against a circumferential surface of the rotating wheel.

In one optional embodiment, the circumferential surface of the rotating wheel is provided with locking portions fitting with the stopping and limiting element.

Multiple locking portions are arranged at intervals along a circumference of the rotating wheel, or

- multiple locking portions are arranged at intervals along an axial direction of the rotating wheel.

In one optional embodiment, an outer tube is mounted on a distal end of the handle, and both the anchor and the transmission tube are inserted into the outer tube.

In one optional embodiment, the handle is provided with a hollow limiting slot, and the hollow limiting slot extends along an axial direction of the outer tube.

The rotating wheel is located inside the hollow limiting slot. The rotating wheel moves along the hollow limiting slot, with a forward stop position and a backward stop position.

In the forward stop position, the rotating wheel moves to the distal end of the hollow limiting slot, with the anchor extending out of the outer tube.

In the backward stop position, the rotating wheel moves to the proximal end of the hollow limiting slot, with the anchor retracting into the outer tube.

In one optional embodiment, an end surface of the distal end of the outer tube is provided with teeth.

In one optional embodiment, the handle is provided with an enclosed chamber, with the limiting element located inside the enclosed chamber.

An unlocking element is mounted between the rotating wheel and the limiting element, wherein the unlocking element is slidingly fitted to the handle along an axial direction of the transmission tube.

When the rotating wheel is screwed and pushed toward the distal end, the transmission tube drives the anchor to rotate and move toward the distal end, and the anchor pulls the traction wire so that the limiting element pushes against the unlocking element to move toward the distal end.

When fixing the rotating wheel and pulling back the unlocking element toward the proximal end, the unlocking element pushes against the limiting element so as to disengage the limiting element from the traction wire.

In one optional embodiment, the unlocking element includes a touch wheel and a tube body connected to the touch wheel.

In an initial state, a distal end of the touch wheel abuts against the rotating wheel, the tube body is inserted into the handle in a sliding manner and sleeved over the transmission tube, and a proximal end of the tube body abuts against the limiting element.

In one optional embodiment, the anchor includes an anchor-head tube, and the traction wire is connected to the anchor-head tube.

A circumferential surface of the anchor-head tube is provided with a helical groove, a helical barb is formed along a circumference of the anchor-head tube, and a distal end of the helical barb is provided with a pointed tip.

In one optional embodiment, the helical barb is provided with a reverse barb directed towards the helical groove and inclined along the helical groove away from the pointed tip.

In one optional embodiment, the anchor further includes a connector, and the connector is connected to the anchor-head tube.

The engaging portion includes a second insertion portion provided on the connector, and the second insertion portion is adapted to the transmission tube.

The connector is provided with an axial through-hole, wherein the traction wire passes through the axial through-hole. A distal end of the traction wire is provided with a protruding head, wherein a protruding head abuts against a distal end of the connector.

In one optional embodiment, a proximal end of the anchor-head tube is provided with a second insertion portion adapted to the transmission tube.

In one optional embodiment, the anchor includes an anchor base and a helical component.

A proximal end of the anchor base is connected to the transmission tube, and a distal end of the anchor base is provided with a pointed tip.

The helical component is connected to the anchor base and extends along a circumference of the anchor base.

In one optional embodiment, the helical component is provided with multiple stopping notches, and the multiple stopping notches are arranged at intervals along a helical direction of the helical component.

In a second aspect, the suturing device provided in the present disclosure includes a winding mechanism, a locking-and-cutting mechanism, and the single-anchor mechanism described in the first aspect.

The traction wire passes through the locking-and-cutting mechanism, and the locking-and-cutting mechanism is configured to lock the traction wire and cut off any excess traction wire.

The embodiments of the present disclosure offer beneficial effects as follows. One end of the traction wire is connected to the anchor, and the traction wire passes through the transmission tube. An end portion of the anchor opposite to the transmission tube is provided with an engaging portion adapted. The limiting element is connected to the traction wire, and the limiting element abuts against an end portion of the transmission tube away from the anchor. By fixing the traction wire by the limiting element and tensioning the traction wire, the anchor and the transmission tube can be maintained in a tight fit through the engaging portion without the need for a key or pin structure, thus making assembly easier. Moreover, by removing the limiting element, the transmission tube can be detached from the traction wire, making the operation more convenient.

To make the above objectives, features, and advantages of the present disclosure more evident and comprehensible, the following preferred embodiments are described in detail with the drawings.

BRIEF DESCRIPTION OF DRAWINGS

In order to more clearly illustrate the specific embodiments of the present disclosure or the technical solution in the relevant art, the drawings required to be used in the description of the specific embodiment or relevant art will be briefly introduced as follows. Obviously, the drawings described below are some embodiments of the present disclosure, for those of ordinary skill in the art, without paying inventive labor, may also obtain other drawings according to these drawings.

REFERENCE NUMERALS

100—anchor; 101—pointed tip; 102—reverse barb; 103—stopping notch; 110—anchor-head tube; 111—helical barb; 120—connector; 121—axial through-hole; 130—anchor base; 140—helical component; 200—transmission tube; 210—spring tube; 220—engaging member; 300—traction wire; 301—protruding head; 400—limiting element; 500—engaging portion; 501—first insertion portion; 502—second insertion portion; 600—sheath; 700—handle; 701—hollow limiting slot; 702—enclosed chamber; 710—stopping and limiting element; 711—first limiting elastic plate; 712—second limiting elastic plate; 713—protrusion; 800—rotating wheel; 801—locking portion; 802—circumferential limiting slot; 810—unlocking element; 811—touch wheel; 812—tube body; 900—outer tube; 901—tooth.

DETAILED DESCRIPTION OF EMBODIMENTS

A clear and complete description of the technical solutions of the present disclosure will be given below in connection with the drawings. Obviously, the described embodiments are a portion of the embodiments of the present disclosure and not all of the embodiments. Based on the embodiments of the present disclosure, all other embodiments obtained by those skilled in the art without inventive effort shall fall within the protection scope of the present disclosure. Without conflict, embodiments and features of embodiments of the present disclosure may be combined with each other.

In the text, "proximal end" and "distal end" are referenced from the perspective of the product operator. The end located outside the body and hand held by the operator is the proximal end; the end that can be implanted into the body of the patient and is away from the operator is the distal end. For those skilled in the art, the specific meanings of the above positional terms in the present disclosure can be understood based on the context.

Figure 1:
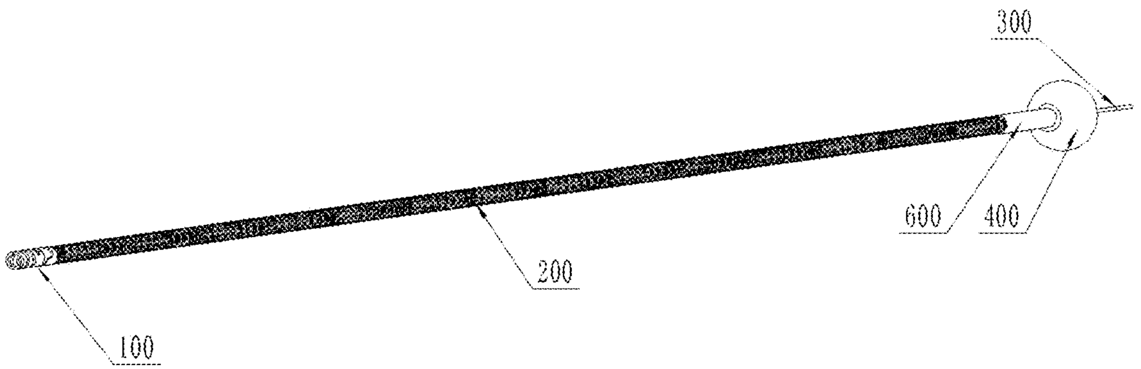
FIG. 1 is a schematic diagram of an anchor, a transmission tube, a traction wire, a limiting element, and a sheath of a single-anchor mechanism according to the embodiments.
Figure 8:
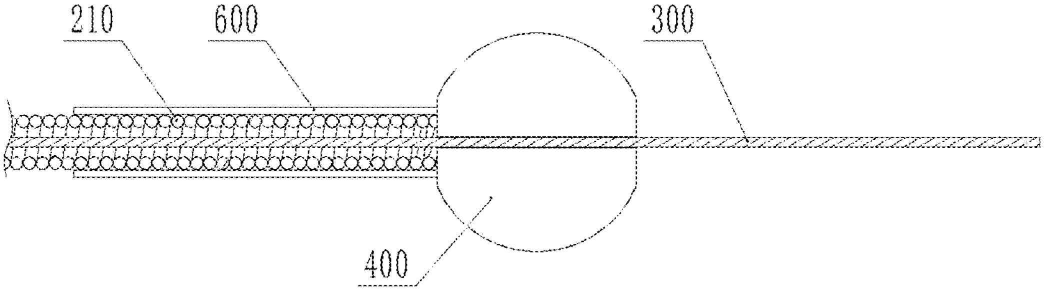
FIG. 8 is a sectional view of a spring tube, a traction wire, a limiting element, and a sheath of the single-anchor mechanism according to the embodiments.
Figure 9:
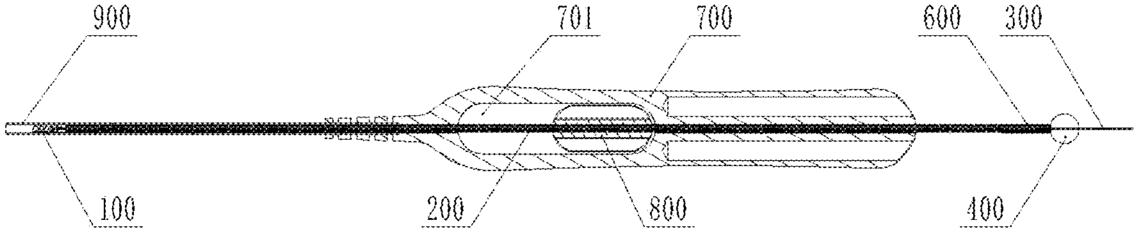
FIG. 9 is a sectional view of the single-anchor mechanism according to the embodiments.

As shown in FIGS. 1, 8, and 9, the embodiment of the present disclosure provides a single-anchor mechanism, including an anchor 100, a transmission tube 200, a traction wire 300, and a limiting element 400. One end of the traction wire 300 is connected to the anchor 100, and the traction wire 300 passes through the transmission tube 200. An end portion of the anchor 100 opposite to the transmission tube 200 is provided with an engaging portion 500 adapted. The limiting element 400 is connected to the traction wire 300, and the limiting element 400 abuts against an end portion of the transmission tube 200 away from the anchor 100.

The position of the anchor 100 is used as the distal end of the transmission tube 200, and the position of the limiting element 400 is used as the proximal end of the transmission tube 200. By pulling the traction wire 300 towards the proximal end and locking the limiting element 400 onto the traction wire 300, the traction wire 300 inside the transmission tube 200 can be kept in a tensioned state. Under the tensioning force of the traction wire 300, the anchor 100 and the transmission tube 200 can be maintained in an engaged state through the engaging portion 500. There is no need to arrange key or pin structures to connect the anchor 100 and the transmission tube 200, thus facilitating the assembly of a single-anchor mechanism. In addition, after the anchor 100 is anchored to the tissue to be sutured, removing the limiting element 400 can allow the transmission tube 200 to be detached from the traction wire 300, thus facilitating subsequent tightening operations of the traction wire 300.

The traction wire 300 can be configured in at least two colors, thus allowing for tightening operations to be performed according to the color. When using multiple sets of single-anchor mechanisms simultaneously, the traction wires 300 with different colors can be configured for multiple anchors 100. During the tightening of the traction wire 300, each anchor 100 corresponds to a specific color of the traction wire 300, thus allowing the operator to easily identify which anchor 100 corresponds to the tightened traction wire 300.

In the embodiment, the limiting element 400 includes a polymer elastic component, wherein the polymer elastic component can be made of materials such as silicone or rubber. The polymer elastic component is provided with a wire-clamping portion, wherein the wire-clamping portion is configured as a wire hole or wire groove. The traction wire 300 passes through the wire-clamping portion and is in interference fit with the wire-clamping portion. The polymer elastic component abuts against the end portion of the transmission tube 200 away from the anchor 100.

When pulling the traction wire 300 towards the proximal end, an external force applied keeps the polymer elastic component abutting the end portion of the transmission tube 200 away from the anchor 100. The wire-clamping portion of the polymer elastic component contracts to clamp and fix the traction wire 300, thereby keeping the traction wire 300 inside the transmission tube 200 tensioned.

In other optional embodiments, the limiting element 400 can be a wire clip or similar device. The limiting element 400 can be detachably connected to the traction wire 300. The limiting element 400 can abut against the end portion of the transmission tube 200 away from the anchor 100, thereby keeping the traction wire 300 inside the transmission tube 200 tensioned.

Figure 2:
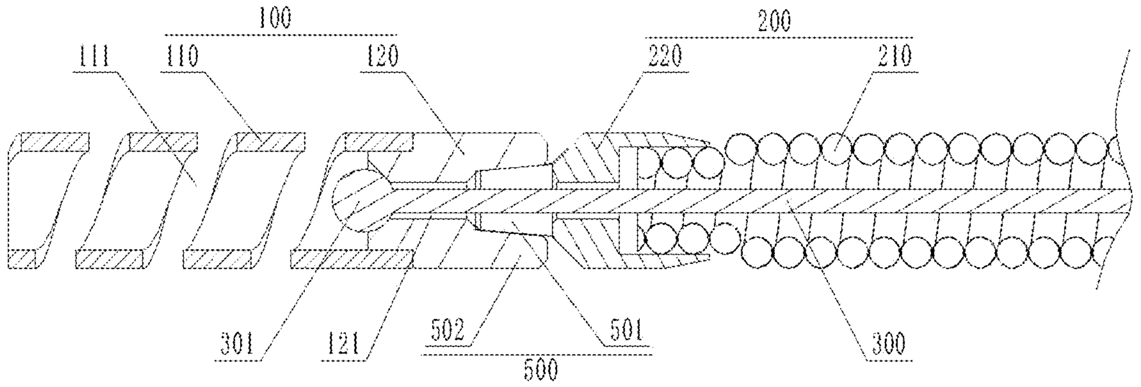
FIG. 2 is a sectional view of the anchor, the transmission tube, the traction wire, and the engaging portion of the single-anchor mechanism according to the embodiments.
Figure 3:
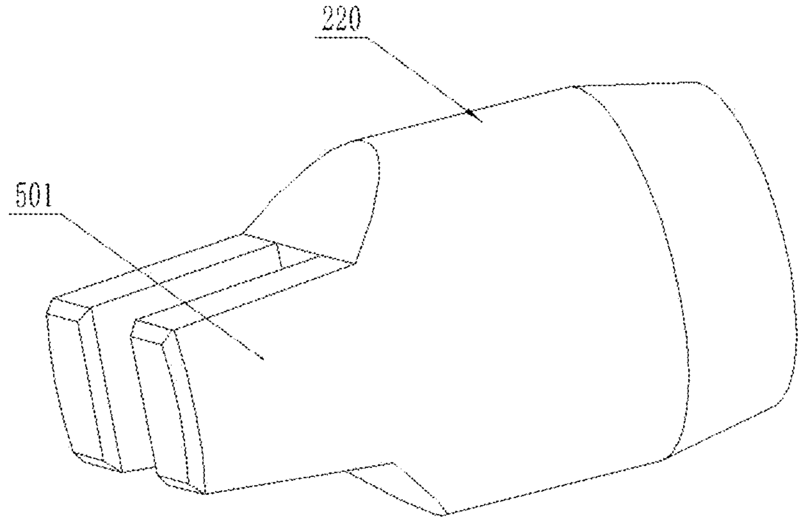
FIG. 3 is a schematic diagram of an engaging member of the single-anchor mechanism according to the embodiments.

As shown in FIGS. 1, 2, and 3, the transmission tube 200 includes a spring tube 210 and an engaging member 220, wherein the engaging member 220 is connected to the spring tube 210. The engaging portion 500 includes a first insertion portion 501 provided on the engaging member 220, wherein the first insertion portion 501 is adapted to a proximal end of the anchor 100.

Specifically, the first insertion portion 501 is configured as a protrusion or slot. By matching the first insertion portion 501 with the anchor 100, a circumferential limitation between the transmission tube 200 and the anchor 100 can be achieved, thus allowing the transmission tube 200 to drive the anchor 100 to rotate synchronously.

As shown in FIGS. 1, 8, and 9, one end of the spring tube 210 away from the engaging member 220 is covered by a sheath 600. The sheath 600 abuts against the limiting element 400.

Specifically, the spring tube 210 can be made of a wire structure, with the sheath 600 covering the end of the spring tube 210 away from the engaging member 220. The sheath 600 provides protection to the spring tube 210, thus preventing the wire material from becoming disordered when the limiting element 400 pushes against the spring tube 210. Therefore, the structural stability of the spring tube 210 can be maintained.

As shown in FIGS. 9, 10, 11, 12, 13, and 14, the single-anchor mechanism further includes a handle 700 and a rotating wheel 800. The transmission tube 200 passes through the handle 700. The transmission tube 200 is connected to the rotating wheel 800, and the rotating wheel 800 is coaxial with the transmission tube 200.

By rotating the rotating wheel 800, the transmission tube 200 can be driven to rotate. When the transmission tube 200 and the anchor 100 are engaged, the transmission tube 200 drives the anchor 100 to rotate synchronously, which allows the anchor 100 to screw into the tissue to be sutured, thereby achieving anchoring.

Referring to FIGS. 11, 12, 13, and 14, the handle 700 is provided with a stopping and limiting element 710, and the stopping and limiting element 710 abuts against a circumferential surface of the rotating wheel 800.

Further, the circumferential surface of the rotating wheel 800 is provided with locking portions 801 fitting with the stopping and limiting element 710.

Figure 11:
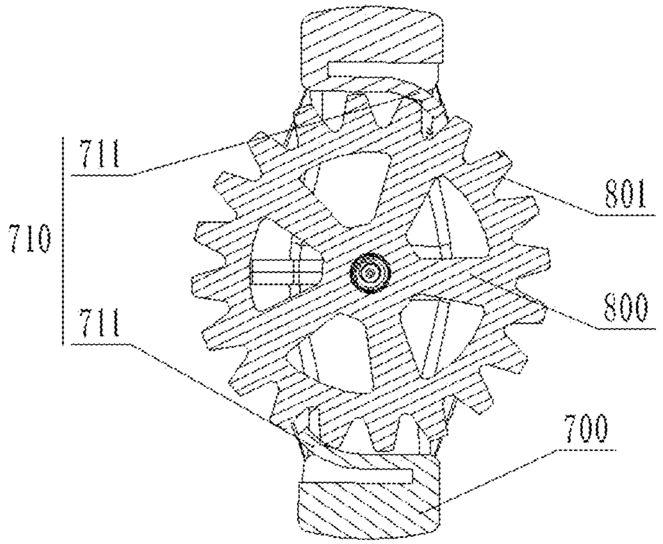
FIG. 11 is a sectional view of a handle and a rotating wheel of the single-anchor mechanism according to the embodiments.
Figure 12:
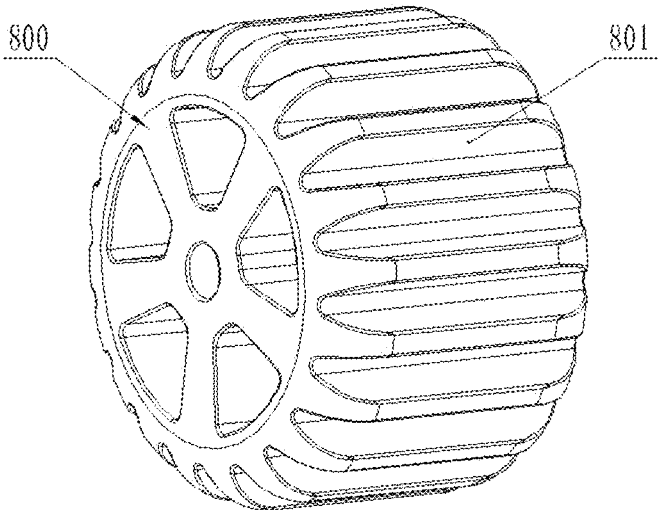
FIG. 12 is a schematic diagram of the rotating wheel in FIG. 11.

As shown in FIGS. 9, 11, and 12, in one embodiment, the locking portion 801 is configured as a groove extending along an axial direction of the rotating wheel 800, with multiple grooves arranged at intervals along a circumference of the rotating wheel 800. The stopping and limiting element 710 includes a first limiting elastic plate 711. During the process where the rotating wheel 800 drives the transmission tube 200 to rotate and drives the anchor 100 to penetrate the tissue to be sutured, the rotation direction of the rotating wheel 800 is defined as the first rotation direction. In the first rotation direction, the first limiting elastic plate 711 inclines toward the axis of the rotating wheel 800. Multiple locking portions 801 are arranged at intervals along a circumference of the rotating wheel 800. When the rotating wheel 800 is turned in the first rotation direction, the first limiting elastic plate 711 elastically deforms to avoid the locking portion 801. Moreover, the first limiting elastic plate 711 can abut against the locking portion 801, thereby preventing the rotating wheel 800 from rotating in the reverse direction.

Figure 13:
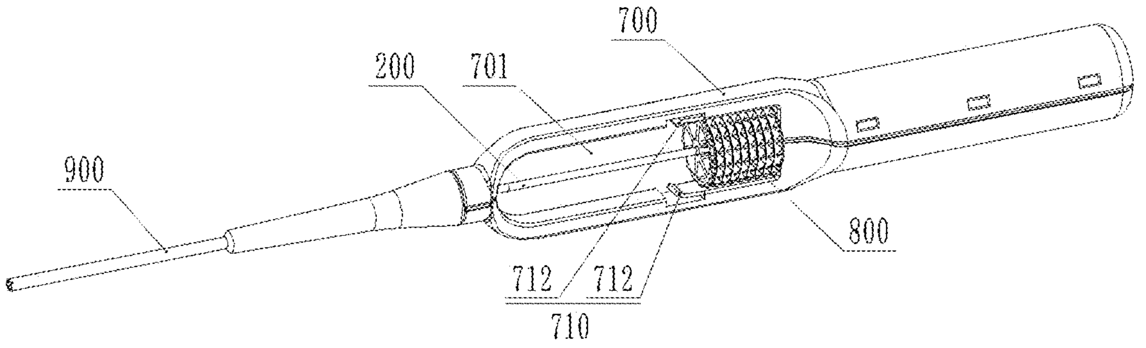
FIG. 13 is a schematic diagram of another handle and rotating wheel of the single-anchor mechanism according to the embodiments.
Figure 14:
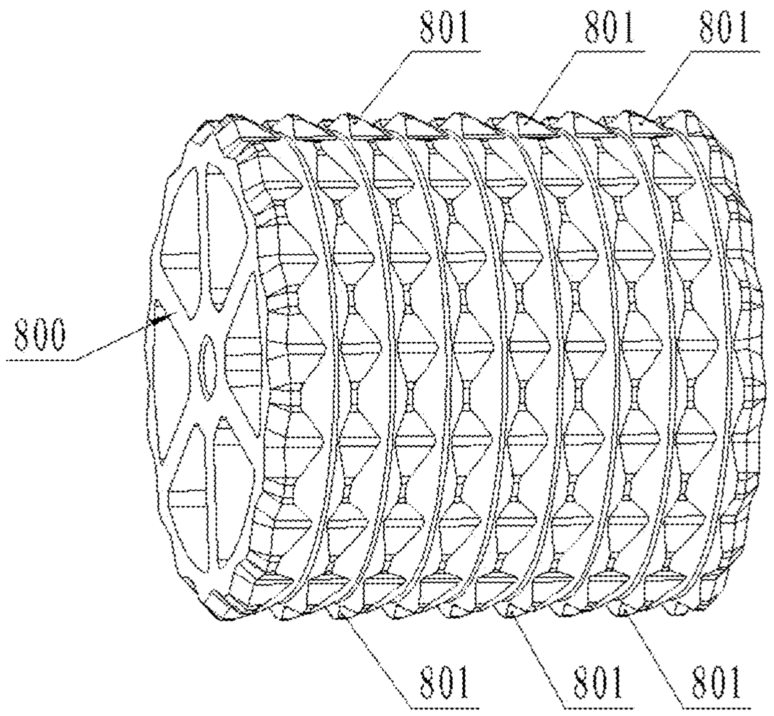
FIG. 14 is a schematic diagram of the rotating wheel in FIG. 13.

As shown in FIGS. 13 and 14, in another embodiment, multiple locking portions 801 are arranged at intervals along an axial direction of the rotating wheel 800. The stopping and limiting element 710 includes a second limiting elastic plate 712, with the distal end of the second limiting elastic plate 712 inclining in a direction proximate to the axis of the rotating wheel 800 from the proximal end to the distal end. The locking portion 801 includes multiple protruding portions, wherein the protruding portion is provided with a beveled surface inclined from the proximal end to the distal end in the direction proximate to the axis of the rotating wheel 800. Multiple protruding portions are arranged at intervals along the axial direction of the rotating wheel 800 to form a group of protrusion sets, and multiple groups of protrusion sets are arranged at intervals along the circumference of the rotating wheel 800. When the rotating wheel 800 is pushed toward the distal end, the protruding portion can push against the second limiting elastic plate 712, causing the second limiting elastic plate 712 to avoid the rotating wheel 800. In addition, the second limiting elastic plate 712 can block the rotating wheel 800 from moving toward the proximal end.

Figure 10:
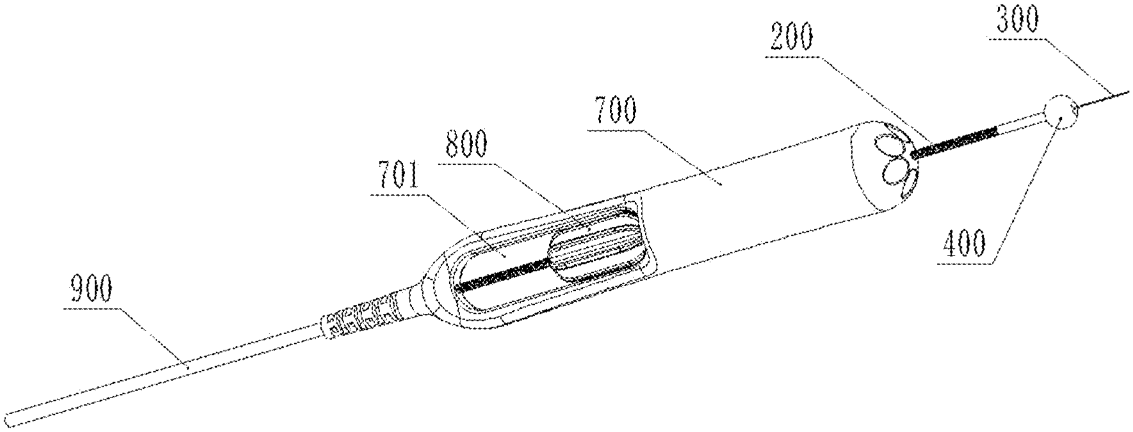
FIG. 10 is a schematic diagram of the single-anchor mechanism according to the embodiments.
Figure 15:
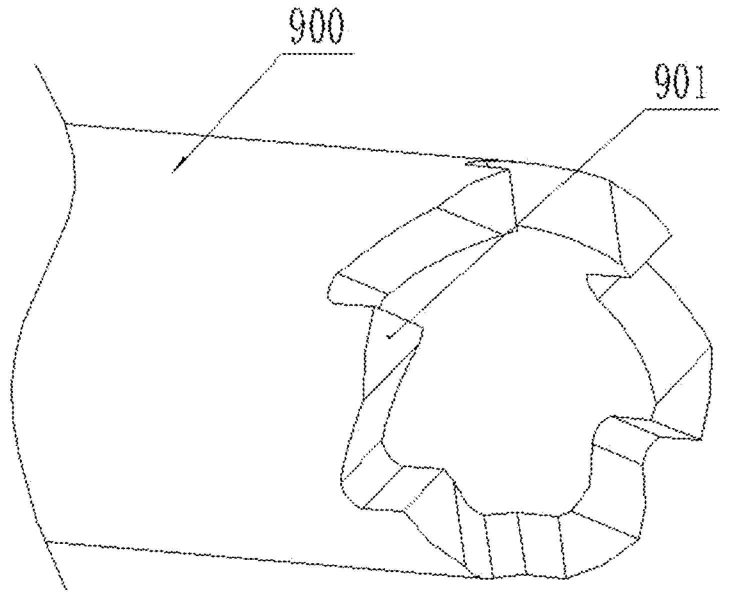
FIG. 15 is a schematic diagram of a distal end of an outer tube of the single-anchor mechanism according to the embodiments.

As shown in FIGS. 9, 10, and 15, an outer tube 900 is mounted on a distal end of the handle 700, and both the anchor 100 and the transmission tube 200 are inserted into the outer tube 900.

During the anchoring operation, first, the distal end of the outer tube 900 is placed against the edge of the wound to be sutured. The handle 700 is held, and the rotating wheel 800 is pushed toward the distal end until the anchor 100 contacts the tissue to be sutured. Then, the rotating wheel 800 is rotated, driving the anchor 100 to rotate synchronously via the transmission tube 200. The anchor 100 can screw into the tissue to be sutured. After anchoring, the handle 700 can be lifted to drive the outer tube 900 away from the wound to be sutured, thus allowing for observation of the depth at which the anchor 100 has entered the tissue to be sutured. The operator uses one hand to keep the rotating wheel 800 and the transmission tube 200 stationary while removing the limiting element 400 with the other hand. This allows for the simultaneous removal of the transmission tube 200, the sheath 600, the handle 700, the rotating wheel 800, and the outer tube 900.

Further, the handle 700 is provided with a hollow limiting slot 701, and the hollow limiting slot 701 extends along an axial direction of the outer tube 900. The rotating wheel 800 is located inside the hollow limiting slot 701. The rotating wheel 800 moves along the hollow limiting slot 701, with a forward stop position and a backward stop position.

In the forward stop position, the rotating wheel 800 moves to the distal end of the hollow limiting slot 701, with the anchor 100 extending out of the outer tube 900. In the backward stop position, the rotating wheel 800 moves to the proximal end of the hollow limiting slot 701, with the anchor 100 retracting into the outer tube 900. The hollow limiting slot 701 restricts the travel of the rotating wheel 800 moving in the axial direction of the transmission tube 200. This can not only limit the penetration depth of the anchor 100 into the tissue to be sutured but also prevent the rotating wheel 800 and the transmission tube 200 from detaching from the handle 700, thereby enhancing structural compactness.

Further, an end surface of the distal end of the outer tube 900 is provided with teeth 901, wherein the multiple teeth 901 are arranged at intervals along the circumference of the outer tube 900. The teeth 901 abuts against the surface of the tissue to be sutured. As the anchor 100 rotates and penetrates the tissue to be sutured, the teeth 901 prevent the tissue to be sutured from rotating with the anchor 100, thereby avoiding the entanglement of mucosal tissue on the anchor 100. Preferably, the teeth 901 can be configured as ratchet teeth, wherein the rotating direction of the ratchet teeth is opposite to the spiral direction of the anchor 100. In other words, the reverse ratchet teeth rotating along the anchor 100 form a pointed tip. Therefore, the ratchet teeth can prevent mucosal tissue from wrapping around the anchor 100.

Figure 16:
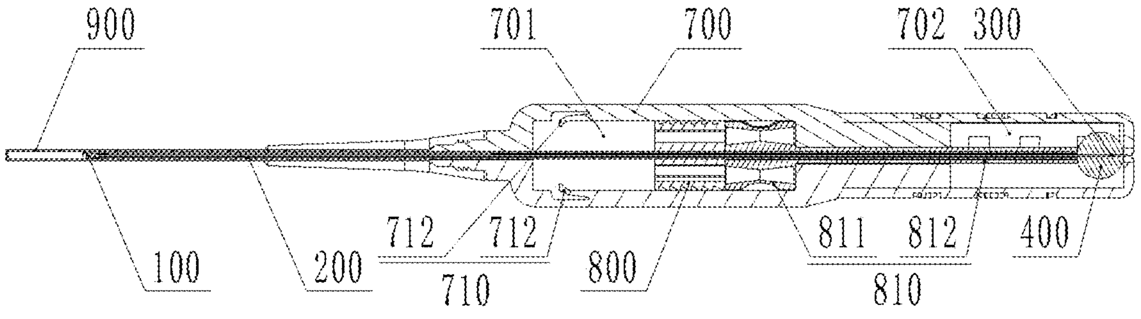
FIG. 16 is a sectional view of another single-anchor mechanism according to the embodiments.
Figure 18:
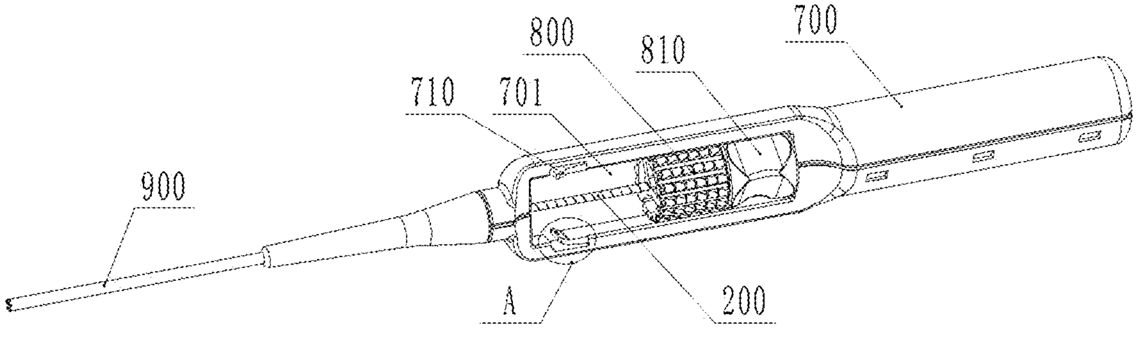
FIG. 18 is a schematic diagram of another single-anchor mechanism according to the embodiments.
Figure 19:
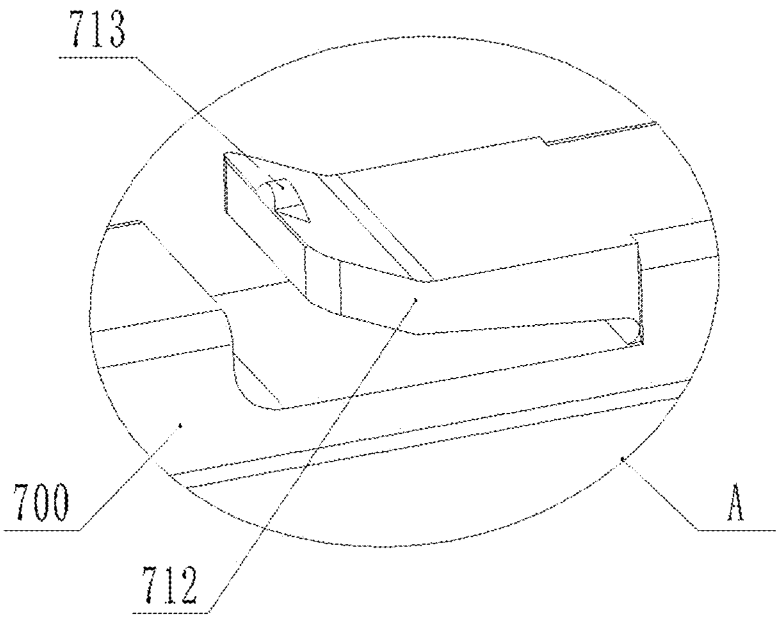
FIG. 19 is a partially enlarged view of position A in FIG. 18.
Figure 20:
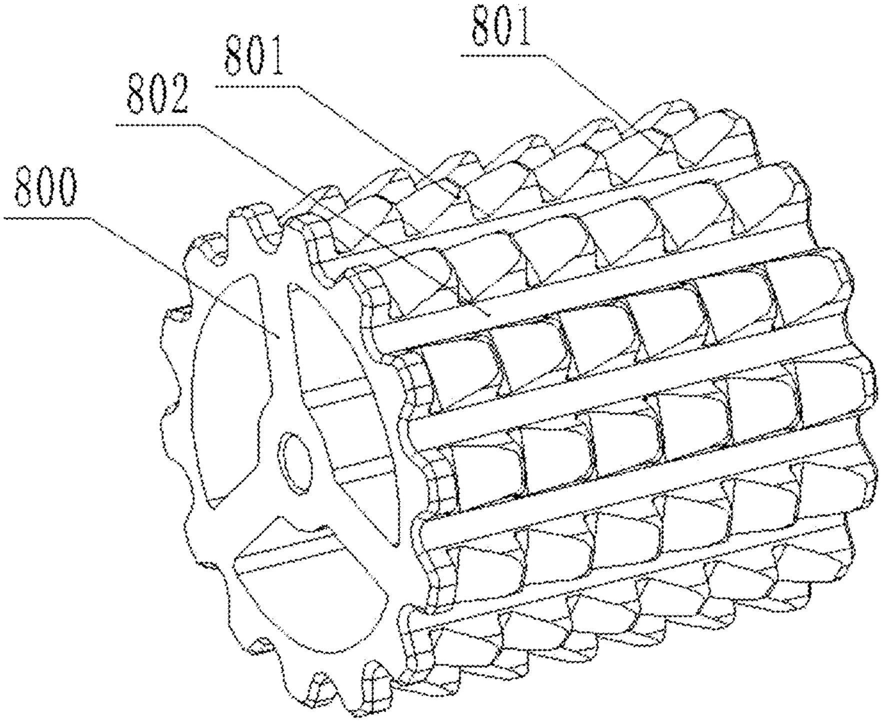
FIG. 20 is a schematic diagram of another rotating wheel of the single-anchor mechanism according to the embodiments.

In one optional embodiment, with reference to FIGS. 16 and 18, the handle 700 is provided with an enclosed chamber 702, with the limiting element 400 located inside the enclosed chamber 702. An unlocking element 810 is mounted between the rotating wheel 800 and the limiting element 400, wherein the unlocking element 810 is slidingly fitted to the handle 700 along an axial direction of the transmission tube 200. When the rotating wheel 800 is screwed and pushed toward the distal end, the transmission tube 200 drives the anchor 100 to rotate and move toward the distal end, and the anchor 100 pulls the traction wire 300 so that the limiting element 400 pushes against the unlocking element 810 to move toward the distal end. When fixing the rotating wheel 800 and pulling back the unlocking element 810 toward the proximal end, the unlocking element 810 pushes against the limiting element 400 so as to disengage the limiting element 400 from the traction wire 300.

The unlocking element 810 can be detachably connected to the rotating wheel 800. When the rotating wheel 800 is screwed and pushed towards the distal end, the transmission tube 200 drives the anchor 100 to penetrate the tissue to be sutured, and the unlocking element 810 moves synchronously towards the distal end with the rotating wheel 800. When it is necessary to withdraw the handle 700, the connection between the unlocking element 810 and the rotating wheel 800, which can be magnetic or snap-fit, is disengaged. The unlocking element 810 is then slid toward the proximal end relative to the handle 700. By the unlocking element 810 pushing the limiting element 400, the limiting element 400 is disengaged from the traction wire 300. At this point, the transmission tube 200, handle 700, rotating wheel 800, unlocking element 810, and outer tube 900 can be removed toward the proximal end along the traction wire 300. Additionally, the unlocking element 810 and the rotating wheel 800 can also be made independent of each other. When the rotating wheel 800 is screwed and pushed towards the distal end, the unlocking element 810 only moves towards the distal end due to the push from the limiting element 400. When the rotating wheel 800 is fixed relative to the handle 700, the unlocking element 810 can be pulled back toward the proximal end, and the limiting element 400 is disengaged by the unlocking element 810.

It should be noted that the limiting element 400 can also be configured to fix the proximal end of the traction wire 300 relative to the limiting element 400 in the form of a knot or a snap-fit. When the unlocking element 810 is pulled back to act on the proximal end of the traction wire 300, the limiting function of the limiting element 400 can be released by cutting off the traction wire 300 or by peeling off the snap-fit.

Figure 17:
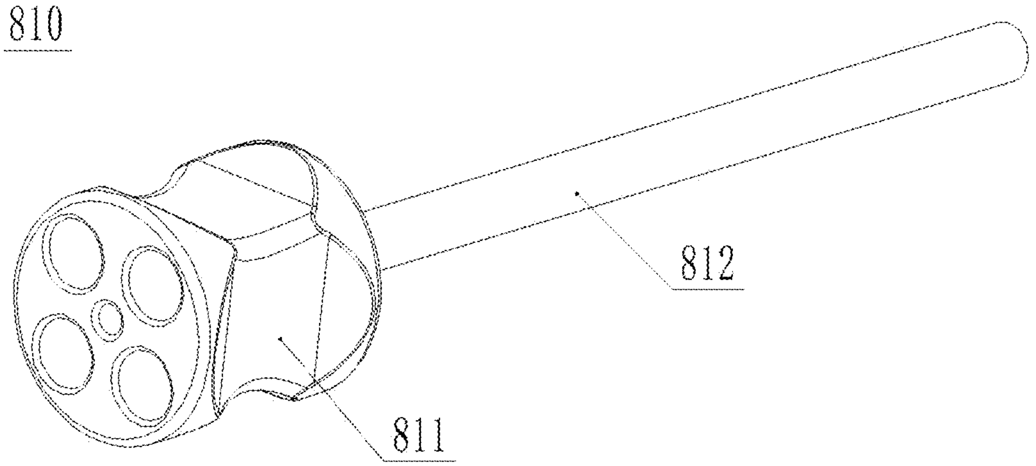
FIG. 17 is a schematic diagram of an unlocking element according to the embodiments.
Figure 21:
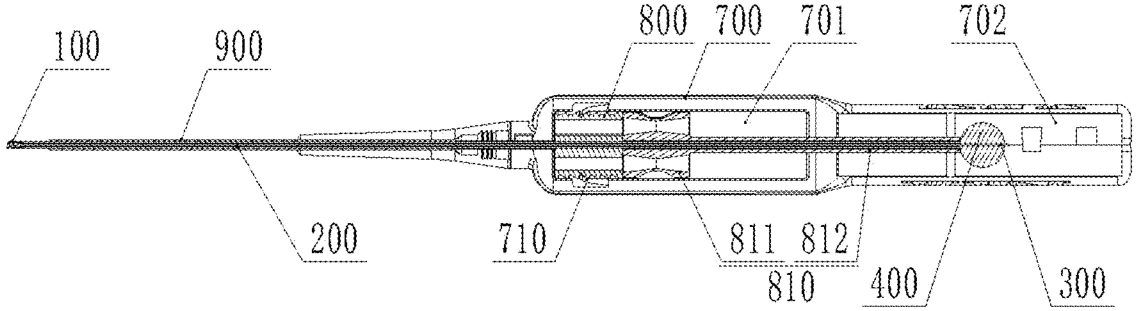
FIG. 21 is a sectional view of the single-anchor mechanism in a state that the anchor is pushed out of the outer tube according to the embodiments.
Figure 22:
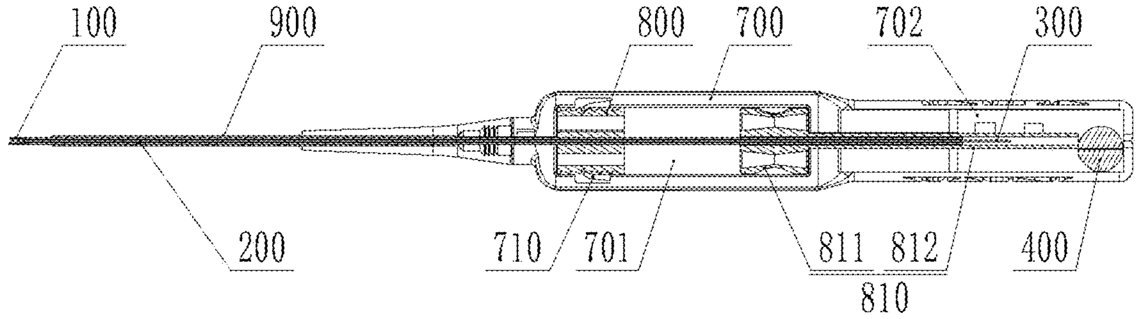
FIG. 22 is a sectional view of the single-anchor mechanism in a state where the limiting element is disengaged from the traction wire according to the embodiments.

In one optional embodiment, with reference to FIGS. 16, 17, and 18, the unlocking element 810 includes a touch wheel 811 and a tube body 812 connected to the touch wheel 811. In an initial state, a distal end of the touch wheel 811 abuts against the rotating wheel 800. The tube body 812 is inserted into the handle 700 in a sliding manner and sleeved over the transmission tube 200. A proximal end of the tube body 812 abuts against the limiting element 400. At this time, the rotating wheel 800 is screwed and pushed towards the distal end. Referring to FIG. 21, the transmission tube 200 drives the anchor 100 to extend from the distal end of the outer tube 900 and penetrate the tissue to be sutured. The anchor 100 pulls the limiting element 400 through the traction wire 300. The limiting element 400 pushes against the tube body 812 toward the distal end, thereby moving the touch wheel 811 toward the distal end in synchronization with the rotating wheel 800. Referring to FIG. 22, after the anchor 100 penetrates the tissue to be sutured, the rotating wheel 800 is fixed relative to the handle 700. By pulling back on the touch wheel 811 toward the proximal end, the tube body 812 will push the limiting element 400 toward the proximal end. In the case where the limiting element 400 is accommodated in the enclosed chamber 702, it can still be made to contact and limit, and the limiting element 400 will not fall outside the handle 700 due to the disengagement from the traction wire 300.

As shown in FIGS. 16, 18, 19, and 20, the rotating wheel 800 can be snapped and locked by a stopping and limiting element 710 arranged on the handle 700, thereby fixing the rotating wheel 800 relative to the handle 700. The stopping and limiting element 710 can be configured as multiple second limiting elastic plates 712, wherein the multiple second limiting elastic plates 712 are distributed around the rotating wheel 800 at intervals. The second limiting elastic plate 712 is provided with an end portion inclined in a direction proximate to the axis of the rotating wheel 800 from the proximal end to the distal end. Additionally, the end portion is provided with a protrusion 713 that protrudes inwardly. The outer surface of the rotating wheel 800 is provided with multiple locking portions 801, wherein the locking portions 801 are divided into several groups. Each group consists of multiple locking portions 801 arranged along the axial direction of the rotating wheel 800. Moreover, an axial limiting slot is formed between any two adjacent locking portions 801. Additionally, multiple groups of locking portions 801 are distributed at intervals along the circumferential limitation of the rotating wheel 800, thus forming circumferential limit slots 802 between any two adjacent groups of locking portions 801. When the rotating wheel 800 is screwed and pushed toward the distal end, the second limiting elastic plate 712 can lock into the axial limiting slot, thus restricting the rotating wheel 800 from receding in an axial direction toward the proximal end. The locking portion 801 is provided with a beveled surface inclined from the proximal end to the distal end in the direction proximate to the axis of the rotating wheel 800. When the rotating wheel 800 is pushed toward the distal end, the second limiting elastic plate 712 can be pushed by the beveled surface, and once the previous locking portion 801 passes over the second limiting elastic plate 712, the second limiting elastic plate 712 rebounds to lock the next locking portion 801. Additionally, when the second limiting elastic plate 712 is locked into the axial limiting slot, the protrusion 713 can be snapped into the circumferential limiting slot 802, thus restricting the rotation of the rotating wheel 800.

As shown in FIGS. 1, 2, 4, and 5, the anchor 100 includes an anchor-head tube 110, wherein the traction wire 300 is connected to the anchor-head tube 110. A circumferential surface of the anchor-head tube 110 is provided with a helical groove. A helical barb 111 is formed along a circumference of the anchor-head tube 110. A distal end of the helical barb 111 is provided with a pointed tip 101. By rotating the anchor-head tube 110, the helical barb 111 can penetrate the tissue to be sutured, and the tissue to be sutured fills the helical groove, thus preventing the anchor 100 from dislodging from the tissue to be sutured.

Further, the helical barb 111 is provided with a reverse barb 102 directed towards the helical groove and inclined along the helical groove away from the pointed tip 101. By the reverse barb 102, the anchor 100 can be hindered from rotating backward. Therefore, this prevents the tissue to be sutured from creeping, which may cause the anchor 100 to come loose.

Figure 4:
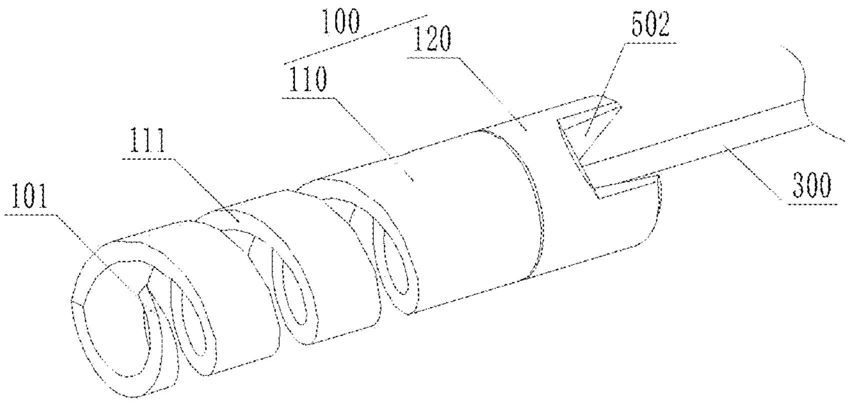
FIG. 4 is a schematic diagram of a first type of anchor, a second insertion portion, and the traction wire of the single-anchor mechanism according to the embodiments.

As shown in FIGS. 2, 3, and 4, the anchor 100 further includes a connector 120, and the connector 120 is connected to the anchor-head tube 110. The engaging portion 500 includes a second insertion portion 502 provided on the connector 120, and the second insertion portion 502 is adapted to the transmission tube 200. The connector 120 is provided with an axial through-hole 121, wherein the traction wire 300 passes through the axial through-hole 121. A distal end of the traction wire 300 is provided with a protruding head 301, wherein the protruding head 301 abuts against a distal end of the connector 120.

The distal end of the traction wire 300 can be bonded to the protruding head 301, or the protruding head 301 can be formed at the distal end of the traction wire 300 in a knotting manner. The diameter of the axial through-hole 121 is smaller than the diameter of the protruding head 301. The connector 120 is welded or bonded to the anchor-head tube 110. When the traction wire 300 is pulled toward the proximal end, the protruding head 301 pushes the connector 120 toward the proximal end and keeps the second insertion portion 502 engaged with the first insertion portion 501.

Figure 5:
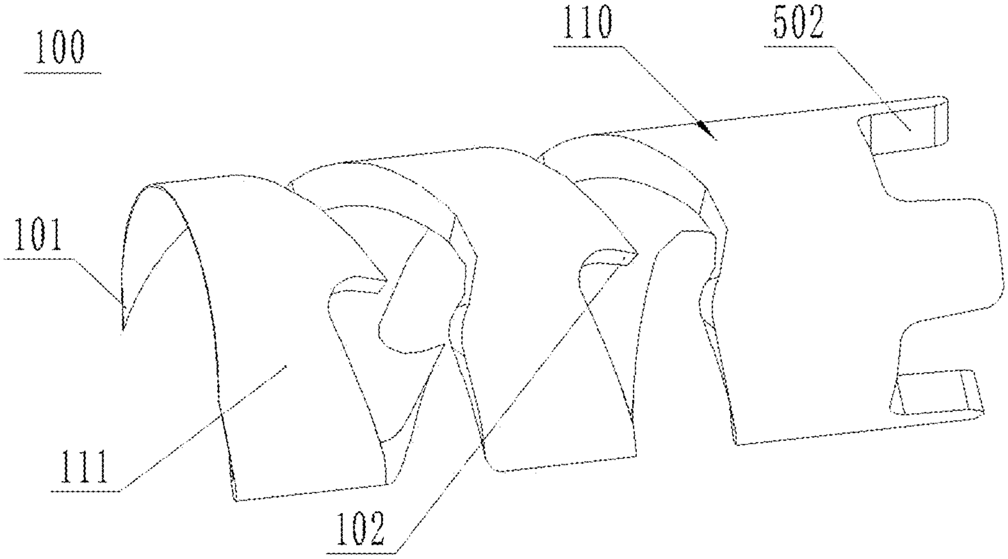
FIG. 5 is a schematic diagram of a second type of anchor of the single-anchor mechanism according to the embodiments.

As shown in FIGS. 1, 2, and 5, in the absence of the connector 120, the proximal end of the anchor-head tube 110 can be provided with the second insertion portion 502 adapted to the transmission tube 200. The second insertion portion 502 is configured as a protrusion or groove. Multiple second insertion portions 502 are provided, and multiple second insertion portions 502 are arranged at intervals along the circumference of the anchor-head tube 110. By fitting the second insertion portion 502 to the transmission tube 200, the transmission tube 200 can drive the anchor-head tube 110 to rotate.

Figure 6:
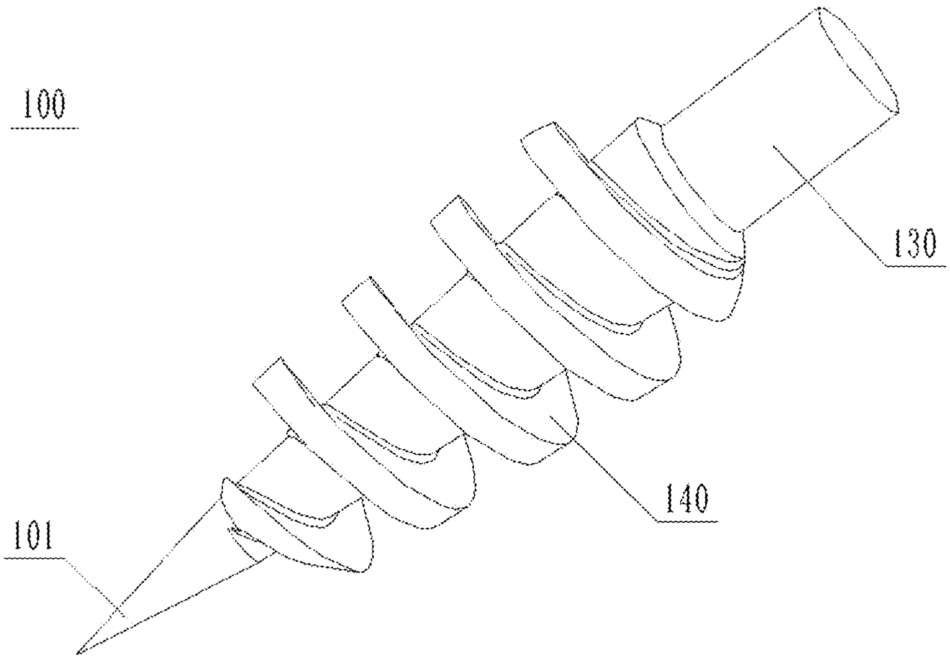
FIG. 6 is a schematic diagram of a third type of anchor of the single-anchor mechanism according to the embodiments.

As shown in FIGS. 6 and 13, the anchor 100 includes an anchor base 130 and a helical component 140. A proximal end of the anchor base 130 is connected to the transmission tube 200, and a distal end of the anchor base 130 is provided with a pointed tip 101. The helical component 140 is connected to the anchor base 130 and extends along a circumference of the anchor base 130. The transmission tube 200 is sleeved over and connected to the proximal end of the anchor base 130. The pointed tip 101 can penetrate the tissue to be sutured. By rotating the anchor 100, the helical component 140 gradually drills into the tissue to be sutured. The helical component 140 can prevent the anchor 100 from dislodging from the tissue to be sutured along the axial direction.

Figure 7:
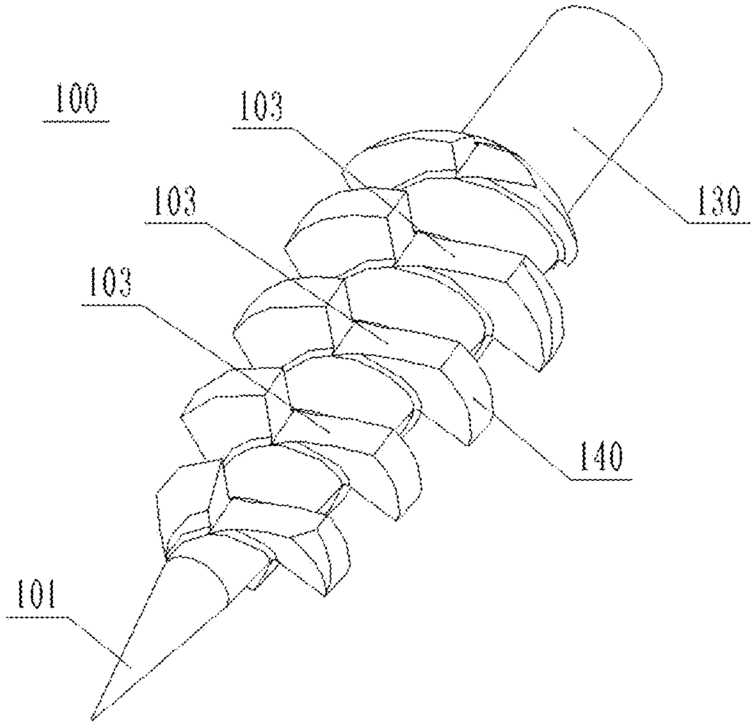
FIG. 7 is a schematic diagram of a fourth type of anchor of the single-anchor mechanism according to the embodiments.

As shown in FIGS. 7 and 13, the helical component 140 is provided with multiple stopping notches 103, and the multiple stopping notches 103 are arranged at intervals along a helical direction of the helical component 140. As the anchor 100 screws into the tissue to be sutured, the tissue rebounds into the stopping notches 103, thus preventing the anchor 100 from rotating in the reverse direction and thus avoiding the anchor 100 from loosening from the tissue to be sutured.

As shown in FIGS. 1, 9, 10, and 13, a suturing device provided in the embodiments of the present disclosure includes a locking-and-cutting mechanism and the single-anchor mechanism described in the above embodiments. The traction wire 300 passes through the locking-and-cutting mechanism, and the locking-and-cutting mechanism is configured to lock the traction wire 300 and cut off any excess traction wire 300.

In embodiments of the present disclosure, the clamping structure of the locking-and-cutting mechanism clamps and fixes the traction wire 300, thereby enabling the locking of the traction wire 300. In addition, the excess traction wire 300 is cut off by cutting. The use of the above-described single-anchor mechanism facilitates the assembly of the single-anchor mechanism and facilitates the anchoring operation of the traction wire 300. The suturing device has the technical effect of the above-described single-anchor mechanism, which will not be repeated herein. Additionally, the suturing device can further include a winding mechanism, wherein the winding mechanism is connected to the traction wire 300. The winding mechanism is configured to pull and tighten the traction wire 300. The winding mechanism employs a winding wheel to rotate so as to wrap the traction wire 300 around the winding wheel, thereby tightening the traction wire 300.

Finally, it should be noted that the above embodiments are intended only to illustrate the technical solutions of the present disclosure and are not intended to be a limitation thereof. Notwithstanding the detailed description of the present disclosure with reference to the foregoing embodiments, it should be understood by those of ordinary skill in the art that one may still modify the technical solution described in the preceding embodiments, or replace some or all of the technical features equally. These modifications or substitutions do not depart the essence of the corresponding technical solution from the scope of the technical solution of the embodiments of the present disclosure.

What is claimed is:

1. A single-anchor mechanism, comprising an anchor, a transmission tube, a traction wire, and a limiting element, wherein one end of the traction wire is connected to the anchor, and the traction wire passes through the transmission tube;

an end portion of the anchor opposite to the transmission tube is provided with an engaging portion; and the limiting element is connected to the traction wire, and the limiting element abuts against an end portion of the transmission tube away from the anchor, wherein the single-anchor mechanism further comprises a handle and a rotating wheel; and the transmission tube passes through the handle, the transmission tube is connected to the rotating wheel, and the rotating wheel is coaxial with the transmission tube.

2. The single-anchor mechanism according to claim 1, wherein the limiting element comprises a polymer elastic component, and the polymer elastic component is provided with a wire-clamping portion;

the traction wire is interference-fitted into the wire-clamping portion; and the polymer elastic component abuts against the end portion of the transmission tube away from the anchor.

3. The single-anchor mechanism according to claim 1, wherein the transmission tube comprises a spring tube and an engaging member, and the engaging member is connected to the spring tube.

4. The single-anchor mechanism according to claim 3, wherein the engaging portion comprises a first insertion portion provided on the engaging member, and the first insertion portion is adapted to a proximal end of the anchor.

5. The single-anchor mechanism according to claim 4, wherein the anchor comprises an anchor-head tube, and the traction wire is connected to the anchor-head tube; and a circumferential surface of the anchor-head tube is provided with a helical groove, a helical barb is formed along a circumference of the anchor-head tube, and a distal end of the helical barb is provided with a pointed tip.

6. The single-anchor mechanism according to claim 5, wherein the helical barb is provided with a reverse barb directed towards the helical groove and inclined along the helical groove away from the pointed tip.

7. The single-anchor mechanism according to claim 5, wherein the anchor further comprises a connector, and the connector is connected to the anchor-head tube;

the engaging portion comprises a second insertion portion provided on the connector, and the second insertion portion is adapted to the transmission tube; and the connector is provided with an axial through-hole, wherein the traction wire passes through the axial through-hole; and a distal end of the traction wire is provided with a protruding head, wherein the protruding head abuts against a distal end of the connector.

8. The single-anchor mechanism according to claim 5, wherein a proximal end of the anchor-head tube is provided with a second insertion portion adapted to the transmission tube.

9. The single-anchor mechanism according to claim 1, wherein the handle is provided with a stopping and limiting element, and the stopping and limiting element abuts against a circumferential surface of the rotating wheel.

10. The single-anchor mechanism according to claim 9, wherein the circumferential surface of the rotating wheel is provided with locking portions fitting with the stopping and limiting element;

multiple locking portions are arranged at intervals along a circumference of the rotating wheel; or, multiple locking portions are arranged at intervals along an axial direction of the rotating wheel.

11. The single-anchor mechanism according to claim 1, wherein an outer tube is mounted on a distal end of the handle, and both the anchor and the transmission tube are inserted into the outer tube.

12. The single-anchor mechanism according to claim 11, wherein the handle is provided with a hollow limiting slot, and the hollow limiting slot extends along an axial direction of the outer tube;

the rotating wheel is located inside the hollow limiting slot; the rotating wheel moves along the hollow limiting slot, with a forward stop position and a backward stop position;

in the forward stop position, the rotating wheel moves to a distal end of the hollow limiting slot, with the anchor extending out of the outer tube; and in the backward stop position, the rotating wheel moves to a proximal end of the hollow limiting slot, with the anchor retracting into the outer tube.

13. The single-anchor mechanism according to claim 11, wherein an end surface of a distal end of the outer tube is provided with teeth.

14. The single-anchor mechanism according to claim 1, wherein the handle is provided with an enclosed chamber, with the limiting element located inside the enclosed chamber;

an unlocking element is mounted between the rotating wheel and the limiting element, wherein the unlocking element is slidingly fitted to the handle along an axial direction of the transmission tube;

when the rotating wheel is screwed and pushed toward a distal end, the transmission tube drives the anchor to rotate and move toward the distal end, and the anchor pulls the traction wire so that the limiting element pushes against the unlocking element to move toward the distal end; and when fixing the rotating wheel and pulling back the unlocking element toward a proximal end, the unlocking element pushes against the limiting element so as to disengage the limiting element from the traction wire.

15. The single-anchor mechanism according to claim 14, wherein the unlocking element comprises a touch wheel and a tube body connected to the touch wheel; and in an initial state, a distal end of the touch wheel abuts against the rotating wheel, the tube body is inserted into the handle in a sliding manner and sleeved over the transmission tube, and a proximal end of the tube body abuts against the limiting element.

16. The single-anchor mechanism according to claim 1, wherein the anchor comprises an anchor base and a helical component;

a proximal end of the anchor base is connected to the transmission tube, and a distal end of the anchor base is provided with a pointed tip; and the helical component is connected to the anchor base and extends along a circumference of the anchor base.

17. The single-anchor mechanism according to claim 16, wherein the helical component is provided with multiple stopping notches, and the multiple stopping notches are arranged at intervals along a helical direction of the helical component.

* * * * *